US009696893B2

(12) United States Patent
Boutoussov et al.

(10) Patent No.: US 9,696,893 B2
(45) Date of Patent: *Jul. 4, 2017

(54) SYSTEM AND METHOD FOR CONTROLLING MULTIPLE LASERS USING A GRAPHICAL USER INTERFACE

(71) Applicant: Biolase, Inc., Irvine, CA (US)

(72) Inventors: Dmitri Boutoussov, Dana Point, CA (US); Glenn Empey, Jr., Laguna Niguel, CA (US); Ryuichi Iwamura, Aliso Viejo, CA (US); Danny Quang Tran, Garden Grove, CA (US)

(73) Assignee: BIOLASE, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/735,020

(22) Filed: Jun. 9, 2015

(65) Prior Publication Data

US 2015/0277738 A1    Oct. 1, 2015

Related U.S. Application Data

(63) Continuation of application No. 13/654,944, filed on Oct. 18, 2012, now Pat. No. 9,052,805.

(60) Provisional application No. 61/549,177, filed on Oct. 19, 2011.

(51) Int. Cl.
*G06F 3/0484* (2013.01)
*G06F 19/00* (2011.01)
*G06F 3/0481* (2013.01)
*G06F 3/0488* (2013.01)

(52) U.S. Cl.
CPC ........ *G06F 3/04847* (2013.01); *G06F 3/0481* (2013.01); *G06F 3/04886* (2013.01); *G06F 19/3406* (2013.01)

(58) Field of Classification Search
None
See application file for complete search history.

(56) References Cited

U.S. PATENT DOCUMENTS 5,877,758 A    3/1999  Seybold
9,052,805 B2   6/2015  Boutoussov et al.
(Continued)

OTHER PUBLICATIONS

Extended European Search Report, Application Serial No. 12841535.3-1972 / 2768421, filed Jun. 18, 2015, by P. Agante da Silva.

*Primary Examiner* — Mahelet Shiberou
(74) *Attorney, Agent, or Firm* — Greenberg Traurig LLP

(57) ABSTRACT

A computer-implemented method for controlling a plurality of electromagnetic energy sources is disclosed. Instructions are executed on a processor to display on a computer-human interface display device a user interface region. The user interface region includes a pie-graph configured to display a total output power of the plurality of the electromagnetic energy sources. The pie-graph includes a radius that indicates the total output power and a plurality of sectors that indicate percentages of the total output power contributed by each of the plurality of the electromagnetic energy sources. An input is received via the user interface region, where the input is an interaction with the pie-graph that changes one of the radius or a sector of the plurality of the sectors. A power output of one or more of the electromagnetic energy sources is adjusted based on the input.

24 Claims, 14 Drawing Sheets

(56) References Cited

U.S. PATENT DOCUMENTS

| | | | |
|---|---|---|---|
| 2006/0064080 A1* | 3/2006 | Cao | A61B 18/22 606/10 |
| 2006/0228687 A1* | 10/2006 | Gomersall | G09B 7/04 434/323 |
| 2007/0255115 A1* | 11/2007 | Anglin, Jr. | G06F 19/3418 600/300 |
| 2009/0002370 A1* | 1/2009 | Helfman | G06T 5/009 345/440 |
| 2010/0251148 A1* | 9/2010 | Brown | F41G 3/32 715/764 |

* cited by examiner

SYSTEM AND METHOD FOR CONTROLLING MULTIPLE LASERS USING A GRAPHICAL USER INTERFACE

CROSS-REFERENCE TO RELATED APPLICATIONS

This is a continuation application of U.S. Non-Provisional application Ser. No. 13/654,944, filed on Oct. 18, 2012, and entitled "System and Method for Controlling Multiple Lasers Using a Graphical User Interface", which claims priority to U.S. Provisional Patent Application No. 61/549,177, filed Oct. 19, 2011, entitled "PiGraph2: New Graphical User Interface for Multiple Laser Devices". The entire contents of these applications are incorporated by reference as is fully set forth herein.

TECHNICAL FIELD

The technology described herein relates generally to a graphical user interface and more particularly to systems and methods for controlling multiple lasers using a graphical user interface.

BACKGROUND

Different electromagnetic energy sources that output different wavelengths of light can be used together in performing various procedures. In the dental field, for example, different wavelengths of light can be effective in performing various aspects of a dental procedure. In one system, electromagnetic radiation of a first wavelength is applied in a teeth-whitening procedure (e.g., output from a laser or laser diode within a wavelength range of approximately 390 nm-480 nm), and electromagnetic radiation of a second wavelength is applied in a gum treatment procedure (e.g., output from a laser or laser diode within a wavelength range of approximately 620 nm-680 nm). The electromagnetic radiation of the different wavelengths may be output simultaneously via a single device. A graphical user interface for controlling the plurality of electromagnetic energy sources used in the device may be desirable.

SUMMARY

A computer-implemented method for controlling a plurality of electromagnetic energy sources is disclosed. In a computer-implemented method for controlling a plurality of electromagnetic energy sources, instructions are executed on a processor to display on a computer-human interface display device a user interface region. The user interface region includes a pie-graph configured to display a total output power of the plurality of the electromagnetic energy sources. The pie-graph includes a radius that indicates the total output power and a plurality of sectors that indicate percentages of the total output power contributed by each of the plurality of the electromagnetic energy sources. An input is received via the user interface region, where the input is an interaction with the pie-graph that changes one of the radius or a sector of the plurality of the sectors. A power output of one or more of the electromagnetic energy sources is adjusted based on the input.

A system for controlling a plurality of electromagnetic energy sources includes one or more processors. The system also includes one or more computer-readable storage mediums containing instructions configured to cause the one or more processors to perform operations. The operations include displaying on a computer-human interface display device a user interface region. The user interface region includes a pie-graph configured to display a total output power of the plurality of the electromagnetic energy sources. The pie-graph includes a radius that indicates the total output power and a plurality of sectors that indicate percentages of the total output power contributed by each of the plurality of the electromagnetic energy sources. The operations further include receiving an input via the user interface region, where the input is an interaction with the pie-graph that changes one of the radius or a sector of the plurality of the sectors. A power output of one or more of the electromagnetic energy sources is adjusted based on the input.

A computer-program product for controlling a plurality of electromagnetic energy sources, tangibly embodied in a machine-readable storage medium, includes instructions configured to cause a data processing apparatus to perform operations. The operations include displaying on a computer-human interface display device a user interface region. The user interface region includes a pie-graph configured to display a total output power of the plurality of the electromagnetic energy sources. The pie-graph includes a radius that indicates the total output power and a plurality of sectors that are configured to indicate percentages of the total output power contributed by each of the plurality of the electromagnetic energy sources. The operations further include receiving an input via the user interface region, where the input is an interaction with the pie-graph that changes one of the radius or a sector of the plurality of the sectors. A power output of one or more of the electromagnetic energy sources is adjusted based on the input.

DETAILED DESCRIPTION

Figure 1:
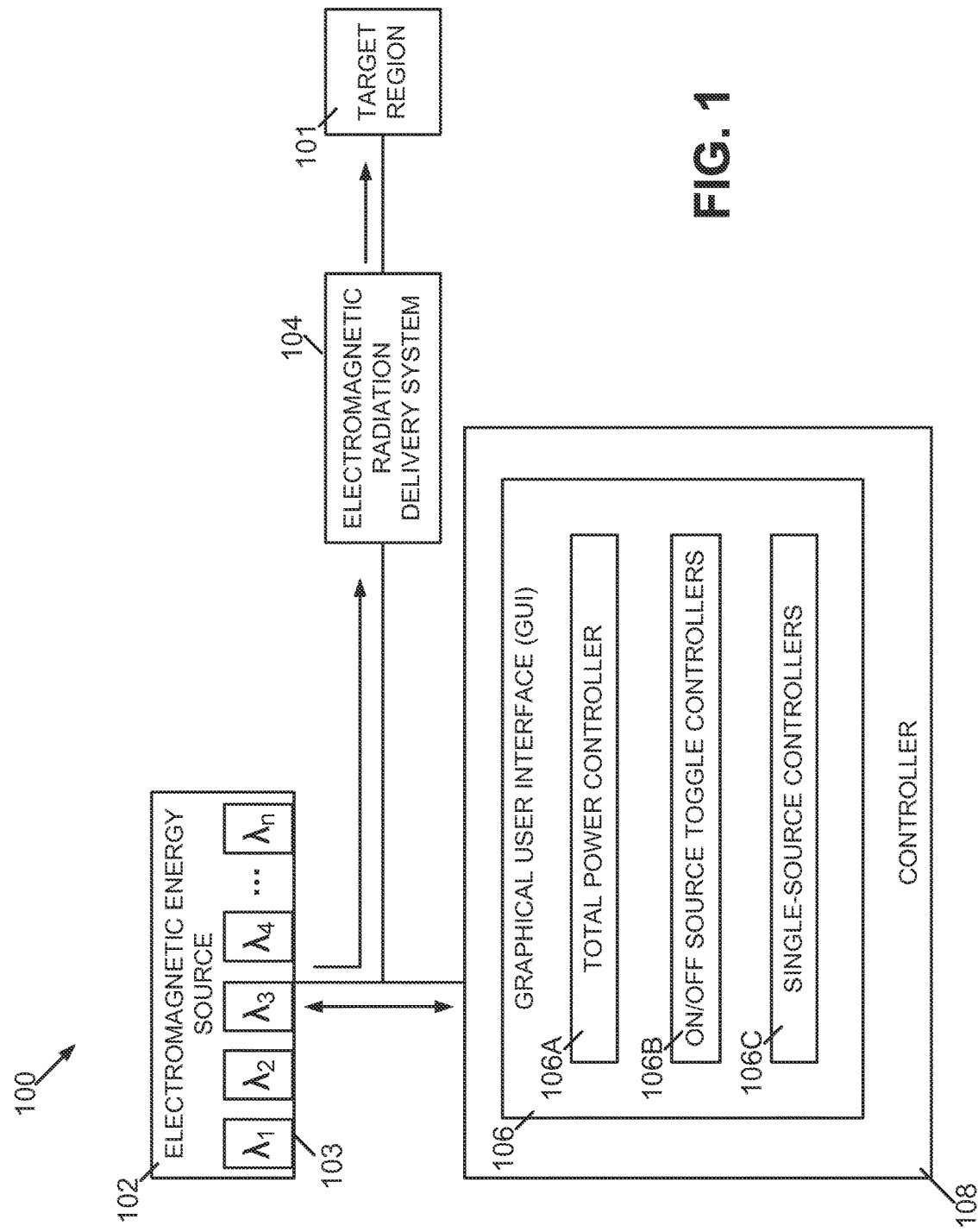
FIG. 1 depicts a block diagram of an example system including a graphical user interface (GUI) for controlling an electromagnetic energy source having a plurality of laser sources.

FIG. 1 depicts a block diagram of an example system 100 including a graphical user interface (GUI) 106 for controlling an electromagnetic energy source 102 having a plurality of laser sources 103. In the system 100 of FIG. 1, the electromagnetic energy source 102 includes n separate laser sources 103 (e.g., solid-state lasers, laser diodes) configured to produce electromagnetic radiation at different wavelengths $\lambda_1, \lambda_2, \lambda_3, \lambda_4, \ldots \lambda_n$. The different wavelengths of the n laser sources 103 may be utilized to perform a variety of different procedures (e.g., simultaneous teeth-whitening and gum treatment in a dental procedure, where the teeth-whitening and the gum treatment procedures each utilize a different wavelength of light). The electromagnetic energy source 102 is connected to both an electromagnetic radiation delivery system 104 and a controller 108. The electromagnetic radiation delivery system 104 routes the electromagnetic energy generated by the n sources 103 to a target region 101. The electromagnetic radiation delivery system 104 may be, for example, one or more multi-mode fiber optic cables configured to guide the output of the n laser sources 103. The electromagnetic radiation delivery system 104 may also be an instrument (e.g., a medical or dental instrument) configured to output the light of the n different wavelengths. The target region 101 is an area to which the electromagnetic energy generated by the n sources 103 is ultimately delivered and may be, for example, an area of the mouth (e.g., an area including teeth and gums) or another area of a human body.

The controller 108 is connected to the electromagnetic energy source 102 and is used to control the output of the n laser sources 103. The controller 108 includes the GUI 106, which includes a total power controller 106A, on/off source toggle controllers 106B, and single-source controllers 106C. The total power controller 106A is configured to display and to allow a user to control a total output power of the n laser sources 103. The total output power of the n laser sources 103 is a combined output power determined by summing the output powers of each of the individual n laser sources 103. The total power controller 106A may be implemented on the GUI 106 via, for example, a pie-graph, where the pie-graph includes a radius that indicates the total output power of the n laser sources 103. The total power controller 106A may allow a user to control the total output power as a percentage of a maximum total output power of the n laser sources 103.

The on/off source toggle controllers 106B and the single-source controllers 106C are each used to control the n laser sources 103 individually. The on/off source toggle controllers 106B include a plurality of toggle buttons or switches, where the toggle button or switch is configured to turn off or turn on a particular source of the n laser sources 103. The single-source controllers 106C are each configured to control the output power of a single one of the n laser sources 103. In one example, each of the plurality of the single-source controllers 106C is configured to control a percentage of the total output power contributed by a single laser source of the n laser sources 103. Each of the single-source controllers 106C may include, for example, a slider control or a set of buttons that enables the user to control the output power contributed by the single laser source of the n laser sources 103.

An input from the user is received via the GUI 106, where the input is an interaction with the total power controller 106A, the on/off source toggle controllers 106B, or the single-source controllers 106C. Based on the input, a power output of one or more of the n laser sources 103 is adjusted. Thus, using various portions of the GUI 106, the user can control the total (i.e., combined) output power of the n laser sources 103, as well as the output power of each of the n sources 103 individually. The electromagnetic energy source 102 may include a variety of different lasers, laser diodes, or other sources of light. The n sources 103 may include, for example, an erbium, chromium, yttrium, scandium, gallium garnet (Er, Cr:YSGG) solid state laser, which generates light having a wavelength in a range of 2.70 to 2.80 μm. The n sources may also include an erbium, yttrium, aluminum garnet (Er:YAG) solid state laser; a chromium, thulium, erbium, yttrium, aluminum garnet (CTE:YAG) solid state laser; an erbium, yttrium orthoaluminate (Er:YAL03) solid state laser; a holmium, yttrium, aluminum garnet (Ho:YAG) solid state laser; a quadrupled neodymium, yttrium, aluminum garnet (quadrupled Nd:YAG) solid state laser; an excimer laser; or a carbon dioxide (CO2) laser.

Figure 2:
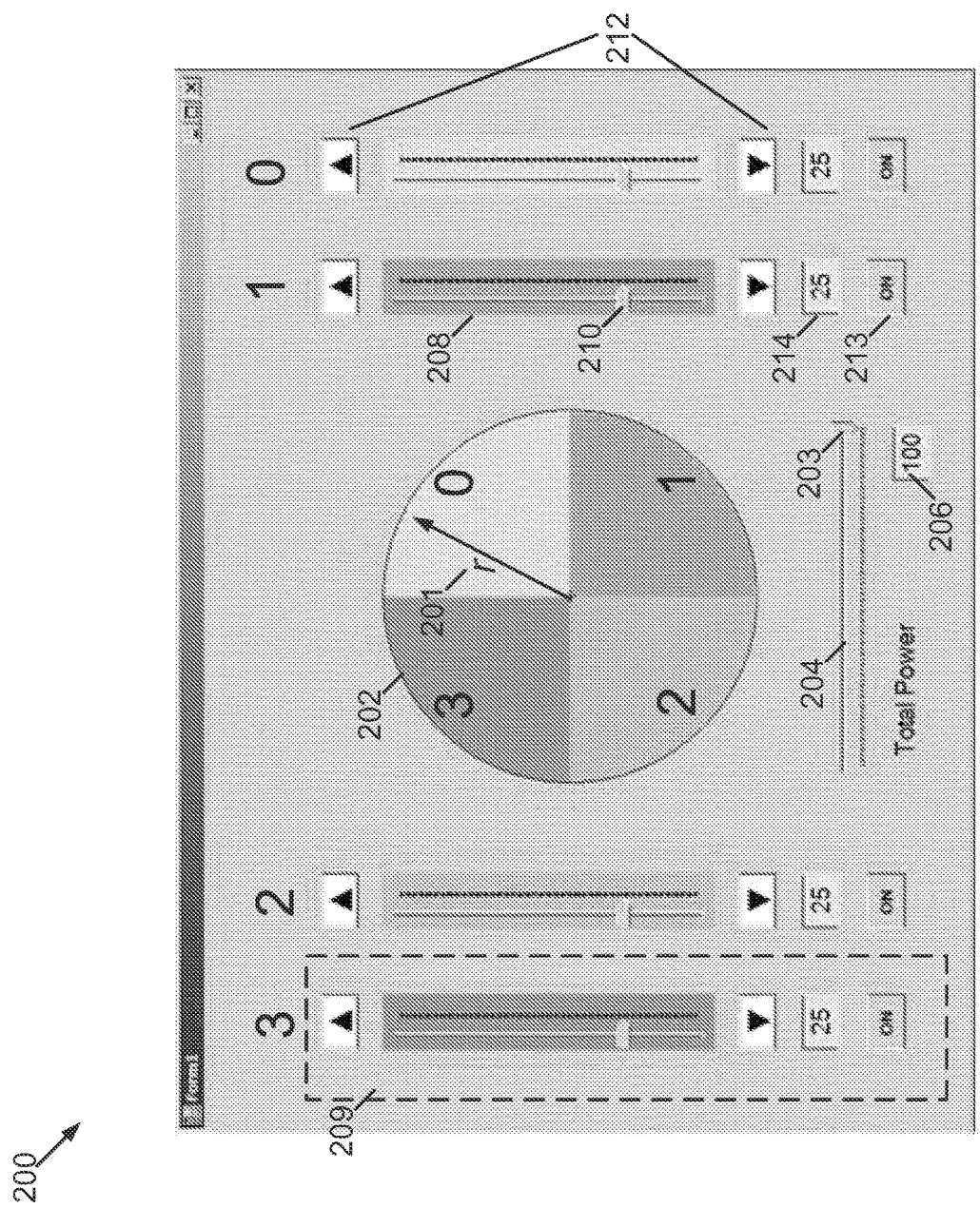
FIG. 2 depicts an example GUI for controlling four electromagnetic energy sources.

FIG. 2 depicts an example GUI 200 for controlling four electromagnetic energy sources. In the GUI 200 of FIG. 2, sectors of a pie-graph 202 and single-source controllers 209 are labeled 0, 1, 2, and 3, and each of the numbered sectors and single-source controllers correspond to one of the four electromagnetic energy sources. The pie-graph 202 is configured to allow a user to control a combined, total output power of the four electromagnetic energy sources. A radius r 201 of the pie-graph indicates the total output power of the four electromagnetic energy sources, such that the pie-graph 202 expands and shrinks as the total output power increases and decreases, respectively. In the example of FIG. 1, the total output power of the four electromagnetic energy sources has a value of 100% of its maximum value, as indicated by a text box 206 that is used to indicate the total output power. Because the total output power is at a maximum value, the radius r 201 of the pie-graph 202 is also at a maximum value.

The user can control the total output power of the four electromagnetic energy sources by changing the radius r 201 of the pie-graph 202. In one example, the radius r 201 of the pie-graph 202 is changed by dragging-and-dropping a point on a circumference of the pie-graph 202. In FIG. 2, because the total output power of the four electromagnetic energy sources is at the maximum value of 100%, the radius r 201 of the pie-graph 202 cannot be increased and can only be decreased to lower the total output power of the four electromagnetic energy sources. As noted above, the GUI 200 of FIG. 2 includes the text box 206 that is used to indicate the total output power of the four electromagnetic energy sources. The text box 206 of FIG. 2 displays a number that indicates the total output power of the four sources as a percentage of a maximum output power for the four sources. In another example, the text box 206 displays a number that indicates the total output power of the four sources as an actual power value in watts.

The GUI 200 further includes total-power slider 204 including a handle 203 that is configured to move along a predetermined path (i.e., a substantially horizontal path in the example of FIG. 2). The user may move the handle 203 of the total power slider 204 along the predetermined path to control the total power output of the four electromagnetic energy sources. A position of the handle 203 along the predetermined path of the total power slider 204 indicates the total output power of the four sources. Thus, a user may control the total output power of the four sources either by manipulating the radius r 201 of the pie-graph 202 or by manipulating the handle 203 of the total-power slider 204. When the total output power is modified via the pie-graph 202 or via the total-power slider 204, other portions of the GUI 200 change correspondingly. For example, the number in the text box 206 and the radius r 201 of the pie-graph 202 change in response to the moving of the handle 203 of the total-power slider 204, and the number in the text box 206 and the position of the handle 203 of the total-power slider 204 change in response to the changing of the radius r 201 of the pie-graph 202.

In one example, the position of the handle 203 or the radius r 201 of the pie-graph 202 change in a manner that is linear with respect to the changes in the total output power, such that, for example, the radius r 201 of the pie-graph 202 is 50% of its maximum length when the total output power of the four electromagnetic energy sources is decreased to 50% of its maximum value. In another example, the position of the handle 203 or the radius r 201 of the pie-graph 202 change in a manner that is not proportional to changes in the total output power of the four sources. In this example, the position of the handle 203 or the radius r 201 of the pie-graph 202 may change according to a logarithmic scale with respect to the changes in the total output power. For example, using a logarithm with base 10, if the maximum total output power is 40 watts, and the total output power has been reduced to 5 watts (i.e., 12.5% of the maximum total output power), then $\log_{10}(40)$ is approximately equal to 1.6, and $\log_{10}(5)$ is approximately equal to 0.7. If the radius r 201 is adjusted according to the logarithm with base 10, the radius r 201 at 5 watts will be 43% of the radius r 201 at 40 watts.

The pie-graph 202 includes a plurality of sectors (i.e., pie pieces) that indicate a percentage of the total output power contributed by each of the four electromagnetic energy sources. In the example of FIG. 2, the sectors of the pie-graph 202 each have an angle of 90 degrees, indicating that each of the four electromagnetic energy sources is contributing an equal amount of power (25%) to the combined total output power of the four sources. A particular, single source of the four electromagnetic energy sources is associated with a particular, single sector of the pie-graph 202, such that the angle of the particular sector indicates the percentage of the total output power contributed by the particular source. Using the GUI 200, the user is able to change the angle of a sector to change the percentage of the total output power contributed by the particular source associated with the sector. In one example, the angle of a particular sector is changed by dragging-and-dropping a point on a partition between the particular sector and a sector adjacent to the particular sector. In another example, the angle of the particular sector is changed by dragging-and-dropping a point within an area of the particular sector.

The GUI 200 of FIG. 2 also includes a plurality of the single-source controllers 209 that are each configured to allow the user to control a percentage of the total output power contributed by a particular source. Changing the percentage of the total output power contributed by the particular source (i.e., via the sectors of the pie-graph 202 or via a single-source controller 209) causes a change in a percentage of the total output power contributed by one or more of the other three electromagnetic energy sources. In one example, changing the percentage of the total output power contributed by the particular source changes an output power for a single other source of the four electromagnetic energy sources. For example, if the percentage of the total output power contributed by source 0 is increased by 10%, the percentage of the total output power contributed by source 1 may be decreased by 10%. In another example, changing the percentage of the total output power contributed by the particular source changes an output power of the three other electromagnetic energy sources (i.e., all of the other sources). For example, if the percentage of the total output power contributed by source 0 is increased by 9%, the percentage of the total output power contributed by sources 1, 2, and 3 may each decrease by 3% (i.e., one third of the increase in percentage of source 0).

Each of the plurality of the single-source controllers 209 includes a single-source slider 208 with a handle 210 that is configured to move along a predetermined path. The user may move the handle 210 along the predetermined path to change the percentage of the total output power contributed by the particular source associated with the slider 208. A position of the handle 210 along the predetermined path of the single-source slider 208 indicates the percentage of the total output power that is contributed by the particular source. The single-source controller 209 further includes a set of buttons 212. The set of buttons 212 includes a first button that is configured to increase the percentage of the total output power contributed by the particular source when pressed and a second button that is configured to decrease the percentage of the total output power contributed by the particular source when pressed. In one example, the set of buttons 212 may be used to perform fine adjustment of the percentage of the total output power contributed by the particular source, while dragging-and-dropping portions of the pie-graph 202 or manipulating the single-source sliders 208 may be used to perform coarse (i.e., rough) adjustment. The set of buttons 212 may adjust the percentage of the total output power contributed by the particular source on a linear scale (i.e., each button press adjusts the percentage by an equal amount) or may adjust the percentage of the total output power in non-linear amounts (e.g., a sequence of five button presses adjusts the percentage by 1%, 2%, 4%, 8%, and 12%, respectively).

Each of the plurality of the single-source controllers 209 also includes a toggle button 213. The toggle button 213 is configured to turn off or turn on the particular source associated with the toggle button 213. The single-source controller 209 also includes a text box 214, where the text box 214 includes a number that indicates the percentage of the total output power contributed by the particular source. In the example of FIG. 2, because each of the four electromagnetic energy sources are contributing an equal amount of power to the total, combined output power, each of the text boxes 214 indicates a value of 25%. A sum of the numbers of the text boxes 214 is equal to 100. In another example, the text box 214 does not display a percentage of the total output power contributed by the particular source but rather indicates an actual output power of the particular source in watts.

In the example GUI 200 of FIG. 2, changing the total output power of the four electromagnetic energy sources (i.e., by adjusting the radius r 201 of the pie-graph 202 or by moving the handle 203 of the total-power slider 204) changes an output power of each of the four electromagnetic energy sources. In one example, changing the total output power by a particular percentage value causes a corresponding change in the output power of each of the four electromagnetic energy sources by the particular percentage value. For example, if the total output power of the four electromagnetic energy sources is adjusted from 100% of the maximum total output power to 50%, the output power of each of the four sources would also be decreased by 50%. In this example, adjusting the total output power does not change the percentage of the total output power contributed by each of the four sources. Thus, in the example of FIG. 2, each of the four sources would continue to contribute 25% of the total output power, notwithstanding the lowering of the total output power to 50% of its maximum value.

The GUI 200 may be used as part of the example system 100 of FIG. 1 and may be used within the controller 108 to control the n laser sources 103 of the electromagnetic energy source 102. Thus, although the example of FIG. 2 illustrates use of the GUI 200 with four electromagnetic energy sources, in other examples, the number of sources is greater than four or less than four. The particular configuration of the GUI 200 depicted in FIG. 2 may represent a "default" setting for controlling a system having four electromagnetic energy sources, where the total output power is set at a maximum value of 100%, and each of the four sources contributes equally to the total output power. Other default settings with non-equal percentages of the total output power contributed by the sources are used in other examples. Further, the GUI 200 may include a number of preset programs that can be loaded from a memory. The preset programs may be used to implement output powers of the four electromagnetic energy sources that are tailored for performing specific procedures. For example, a preset program may be loaded in the GUI 200 for performing a specific dental procedure. The specific dental procedure may use the different sources having the different wavelengths to perform a variety of oral cleaning and disinfection actions simultaneously. The variety of oral cleaning and disinfection actions may use, for example, laser light at wavelengths of 810 nm, 940 nm, and 980 nm to perform teeth cleaning, teeth whitening, bacteria removal, gum treatment, composite curing, or various other actions.

Other modifications may be made to the GUI 200 of FIG. 2. In one system, the single-source sliders 208 may be eliminated, such that only the buttons 212 and the pie-graph 202 may be used to adjust the percentage of the total output power contributed by a particular source. In another example system, up/down buttons that adjust the total output power of the four sources are included. Although the pie-graph 202 of FIG. 2 is depicted as being circular in shape, in other examples, the pie-graph 202 is of a variety of different shapes (e.g., oval, square, or any other shape).

Figure 3:
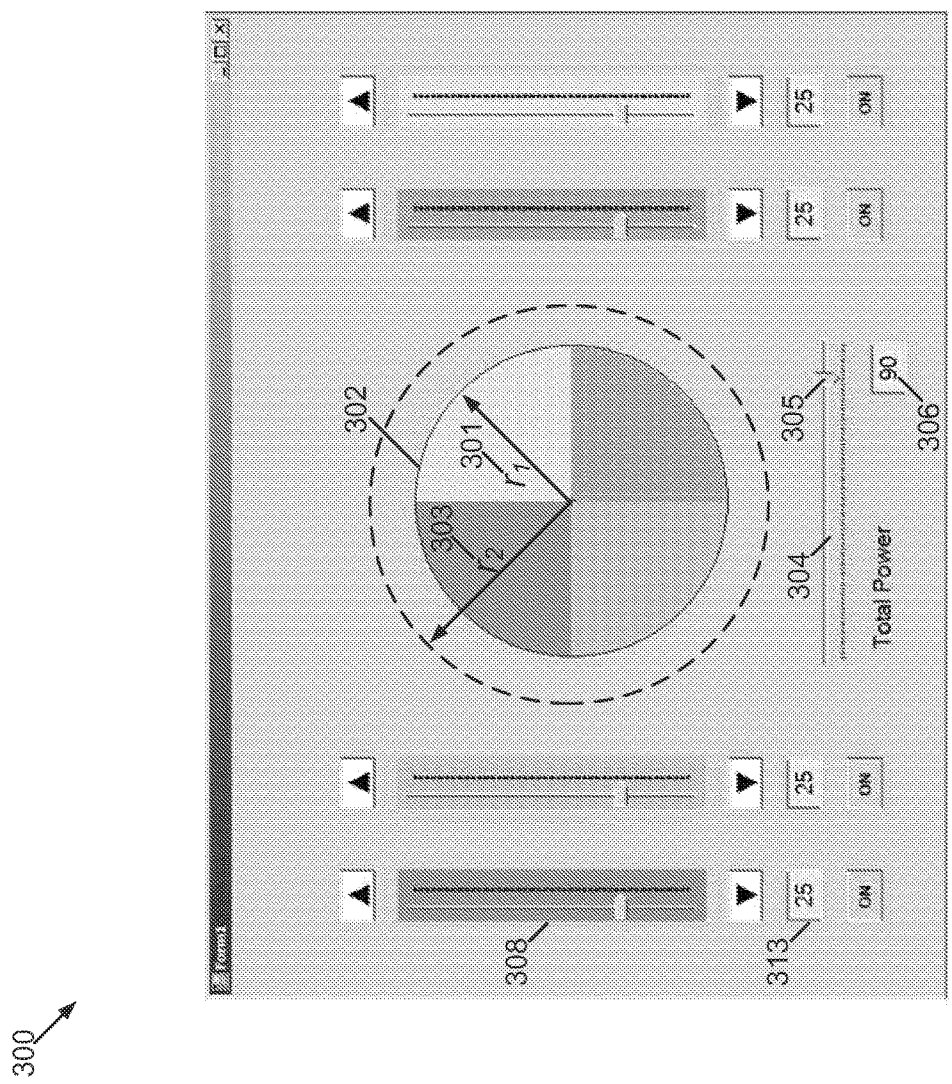
FIG. 3 depicts an example GUI including a pie-graph having a radius that indicates a combined, total output power of four electromagnetic energy sources.

FIG. 3 depicts an example GUI 300 including a pie-graph 302 having a radius $r_1$ 301 that indicates a combined, total output power of four electromagnetic energy sources. In the example GUI 300 of FIG. 3, the combined, total output power of the four electromagnetic energy sources has been decreased from 100% of a maximum total output power to 90% of the maximum total output power. This is indicated in a text box 306 that is configured to indicate the total output power, where a number in the text box indicates that the total output power is 90% of the maximum total output power of the four electromagnetic energy sources. The decreased total output power is also indicated in a total-power slider 304, where a handle of the total-power slider 304 is moved from a right-most position of the slider 304 to another position 305 that is indicative of the total output power being 90% of the maximum total output power.

The 90% total output power is also indicated by the radius $r_1$ 301 of the pie-graph 302. The radius $r_1$ 301 is smaller than a radius $r_2$ 303, where the radius $r_2$ 303 is the radius of the pie-graph 302 when the total output power is set to 100% of the maximum total output power. The total output power may have been adjusted in the example of FIG. 3 either by moving the handle of the total-power slider 304 to its position 305 (e.g., via a drag-and-drop procedure) or by changing the radius $r_1$ 301 of the pie-graph 302 (e.g., by dragging-and-dropping a point on a circumference of the pie-graph 302).

In the example GUI 300 of FIG. 3, changing the total output power of the four electromagnetic energy sources from 100% to 90% does not change a percentage of the total output power contributed by each of the four sources. A text box 313 included on a single-source controller for each of the four electromagnetic energy sources indicates that each source is contributing 25% of the total output power, and a position of a handle on each single-source slider 308 indicates the same. Although the percentage of the total output power contributed by each of the four electromagnetic energy sources is not changed when the total output power is changed, an actual output power for each source changes. Changing the total output power by a particular percentage value causes a corresponding change in the actual output power of each of the four electromagnetic energy sources by the particular percentage value. Thus, in FIG. 3, adjusting the total output power from 100% to 90% causes each of the four sources to output 90% of the power that the source was outputting when the total output power was at 100%. For example, if the total output power was 40 watts when the four sources were outputting 100% of the maximum total output power, and each of the four sources were contributing 25% of the total output power (10 watts each), then adjusting the total output power to 90% of the maximum total output power causes the total output power to drop to 36 watts, with each source continuing to contribute 25% of the total output power (9 watts each).

Figure 4:
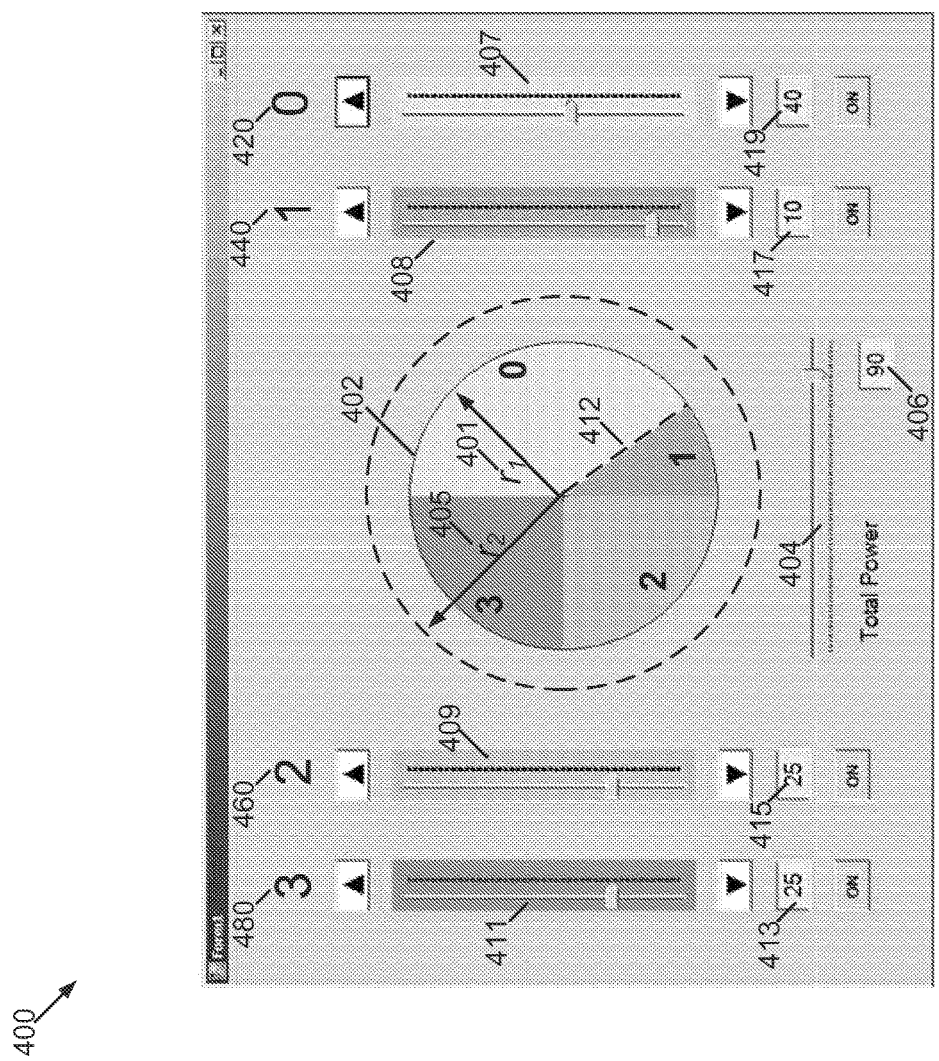
FIG. 4 depicts an example GUI with single-source controllers for four electromagnetic energy sources, where changing a percentage of a total output power contributed by a particular source causes a corresponding power change in a single other source.

FIG. 4 depicts an example GUI 400 with single-source controllers for four electromagnetic energy sources, where changing a percentage of a total output power contributed by a particular source causes a corresponding power change in a single other source. In the example GUI 400 of FIG. 4, the total power output of the four electromagnetic energy sources is at 90% of a maximum total output power for the four sources. This is indicated at a text box 406 indicating the total output power as a percentage of the maximum total output power for the four sources. The total output power at 90% is also indicated in a total-power slider 404, which includes a handle having a position that indicates a total output power of 90% of the maximum total output power for the four electromagnetic energy sources. The total output power of 90% is further illustrated in a pie-graph 402 having a radius $r_1$ 401 that is less than a radius $r_2$ 405. The radius $r_2$ 405 is the radius of the pie-graph 402 when the total output power is at 100% of the maximum total output power.

In the example GUI 400 of FIG. 4, four single-source controllers 420, 440, 460, 480 are labeled 0, 1, 2, and 3, respectively. Each of the four single-source controllers 420, 440, 460, 480 is associated with a particular source of the four electromagnetic energy sources and is configured to control the percentage of the total output power contributed by the particular source. In the GUI 400, changing the percentage of the total output power contributed by the particular source by a particular percentage value causes a corresponding power change in a single other source. Specifically, the corresponding power change is a change of the particular percentage value, but of an opposite magnitude. Thus, in FIG. 4, the single source controller 420 is associated with electromagnetic energy source 0, and a percentage of the total output power contributed by source 0 has been increased from 25% to 40%, as indicated at text box 419 and at single-source slider 407. The increase in the percentage of the total output power contributed by the source 0 was implemented either by moving a handle of the single-source slider 407, by dragging-and-dropping a point on a partition 412 that separates sectors of the pie-graph 402, or by using a set of buttons of the single-source controller 420.

Changing the percentage of the total output power contributed by source 0 causes the corresponding power change in electromagnetic energy source 1, as indicated at single-source controller 440. In the single-source controller 440, a text box 417 indicates that a percentage of the total output power contributed by the source 1 has decreased from 25% to 10%. The decrease of 15% is tied to the increase of 15% that occurred in source 0. The single-source controller 440 further indicates the corresponding power change via a position of a handle of a single-source slider 408, which has been automatically adjusted downward to indicate the decrease in 15% of the percentage of the total output power contributed by source 1. Thus, adjusting the percentage of the total output power contributed by the source 0 causes an automatic change in the percentage of the total output power contributed by the source 1.

A percentage of the total output power contributed by sources 2 and 3 are not affected by the adjustment to the percentage of the total output power contributed by source 0, as indicated at sliders 409, 411 and text boxes 413, 415 of single-source controllers 460, 480. A sum of the numbers of the four text boxes 413, 415, 417, 419 for the single-source controllers 420, 440, 460, 480 is equal to 100. Although the example of FIG. 4 illustrates that adjusting the percentage of the total output power contributed by a particular source causes a corresponding power change in a single other source of the four electromagnetic energy sources, in other examples, multiple other sources are affected by adjusting the power contributed by the particular source. For example, in other GUI systems, changing the percentage of the total output power contributed by the source 0 causes a change of a percentage of the total output power contributed by each of the other three sources of the plurality of the electromagnetic energy sources. Thus, if the percentage of the total output power contributed by source 0 was increased by 15%, as in the example of FIG. 4, the percentage of the total output power contributed by sources 1, 2, and 3 would each be decreased by an equal amount, 5% (i.e., the increase of 15% that occurred in source 0 divided by the number of other sources).

Figure 5:
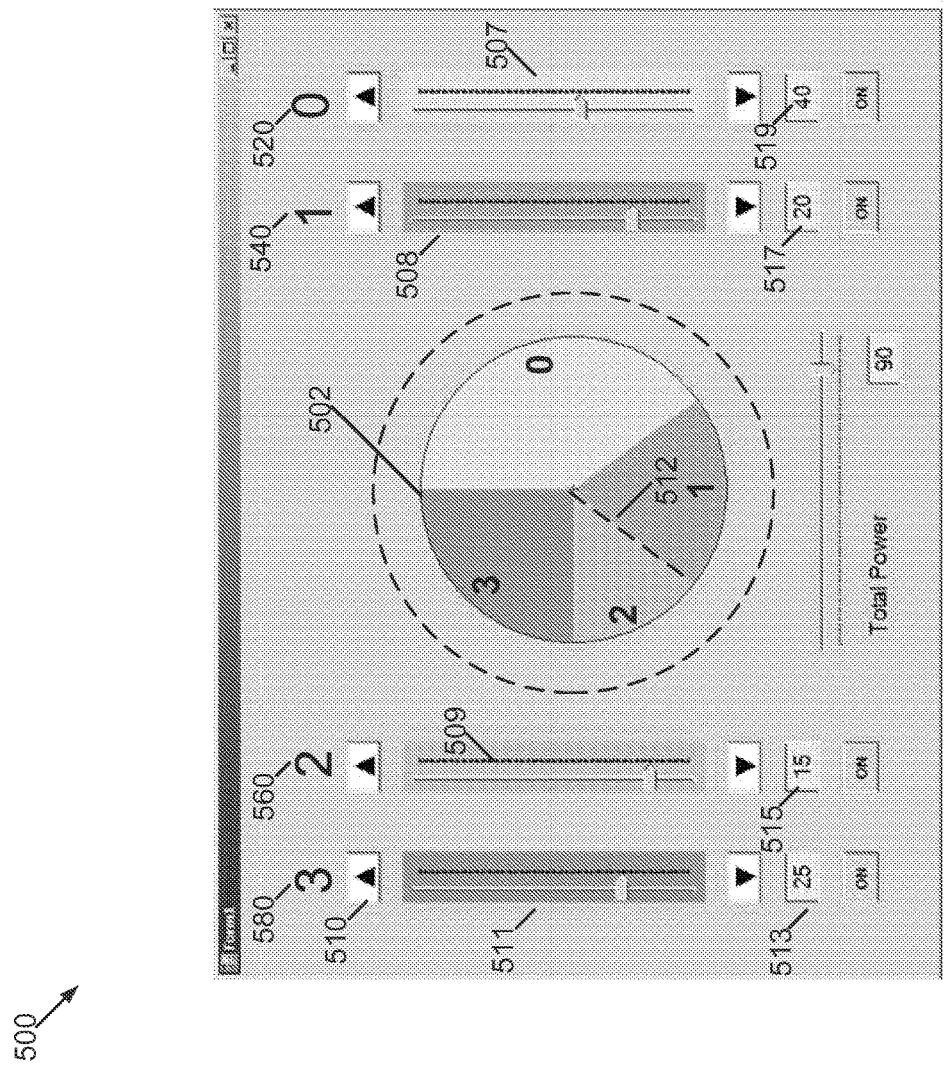
FIG. 5 depicts an example GUI and illustrates an effect of changing a percentage of a total output power contributed by a single electromagnetic energy source.

FIG. 5 depicts an example GUI 500 and illustrates an effect of changing a percentage of a total output power contributed by a single electromagnetic energy source. In the example GUI 500 of FIG. 5, four single-source controllers 520, 540, 560, 580 are labeled 0, 1, 2, and 3, respectively, and are associated with electromagnetic energy sources having these number designations. In the example of FIG. 5, the single source controller 540 corresponds to electromagnetic energy source 1, and a percentage of the total output power contributed by source 1 has been increased from 10% to 20%, as indicated at text box 517 and single-source slider 508. The increase in the percentage of the total output power contributed by the source 1 was implemented either by moving a handle of the single-source slider 508, by dragging-and-dropping a point on a partition 512 that separates sectors of the pie-graph 502, or by using a set of buttons of the single-source controller 540.

Changing the percentage of the total output power contributed by source 1 causes a corresponding power change in electromagnetic energy source 2, as indicated at single-source controller 560. In the single-source controller 560, a text box 515 indicates that a percentage of the total output power contributed by the source 2 has decreased from 25% to 15%. The drop of 10% corresponds to the increase of 10% that occurred in source 1. The single-source controller 560 further indicates the corresponding power change via a position of a handle of a single-source slider 509, which has been automatically adjusted downward to indicate the decrease in 10% of the percentage of the total output power contributed by source 2. A percentage of the total output power contributed by sources 3 and 0 are not affected by the adjustment to the percentage of the total output power contributed by source 1, as indicated at sliders 507, 511 and text boxes 513, 519 of single-source controllers 520, 580.

Figure 6:
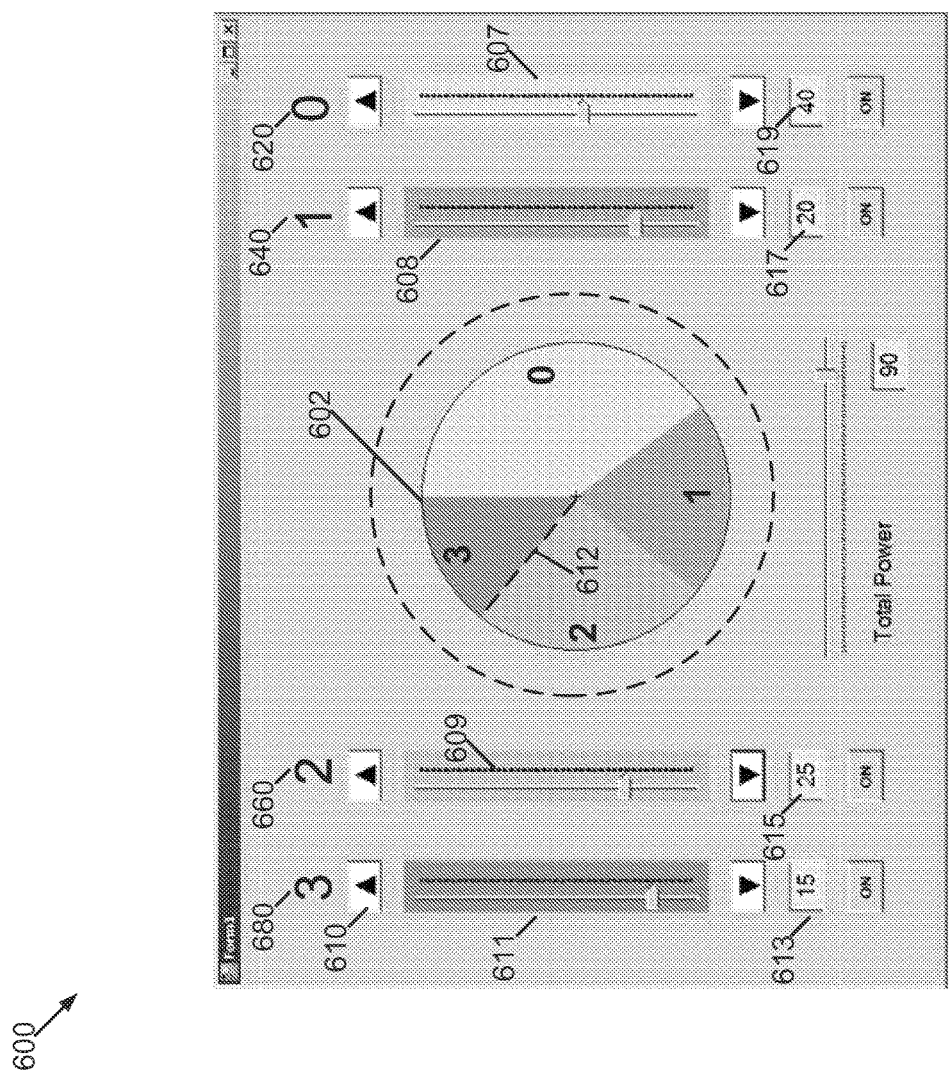
FIG. 6 depicts another example GUI and illustrates an effect of changing a percentage of a total output power contributed by a single source.

FIG. 6 depicts another example GUI 600 and illustrates an effect of changing a percentage of a total output power contributed by a single source. In the example GUI 600 of FIG. 6, four single-source controllers 620, 640, 660, 680 are labeled 0, 1, 2, and 3, respectively, and are associated with electromagnetic energy sources having these number designations. In the example of FIG. 6, the single source controller 660 corresponds to electromagnetic energy source 2, and a percentage of the total output power contributed by source 2 has been increased from 15% to 25%, as indicated at text box 615 and single-source slider 609. The increase in the percentage of the total output power contributed by the source 2 was implemented either by moving a handle of the single-source slider 609, by dragging-and-dropping a point on a partition 612 that separates sectors of pie-graph 602, or by using a set of buttons of the single-source controller 660.

Changing the percentage of the total output power contributed by source 2 causes a corresponding power change in electromagnetic energy source 3, as indicated at single-source controller 680. In the single-source controller 680, a text box 613 indicates that a percentage of the total output power contributed by the source 3 has decreased from 25% to 15%. The drop of 10% corresponds to the increase of 10% that occurred in source 2. The single-source controller 680 further indicates the corresponding power change via a position of a handle of a single-source slider 611, which has been automatically adjusted downward to indicate the decrease in 10% of the percentage of the total output power contributed by source 3. A percentage of the total output power contributed by sources 0 and 1 are not affected by the adjustment to the percentage of the total output power contributed by source 2, as indicated at sliders 607, 608 and text boxes 617, 619 of single-source controllers 620, 640.

The GUIs 400, 500, 600 of FIGS. 4-6 illustrate example systems where the electromagnetic energy sources are connected conceptually in a "clockwise" arrangement, such that an adjustment to the percentage of the total output power contributed by a particular source only causes a change in output power for a single other source that is adjacent to the particular source in a clockwise direction. Thus, if the electromagnetic energy sources are numbered 0, 1, 2, and 3, as in FIGS. 4-6, a power change in source 0 affects only a power output of source 1, a power change in source 1 affects only a power output of source 2, a power change in source 2 affects only a power output of source 3, and a power change in source 3 affects only a power output of source 0.

Figure 7:
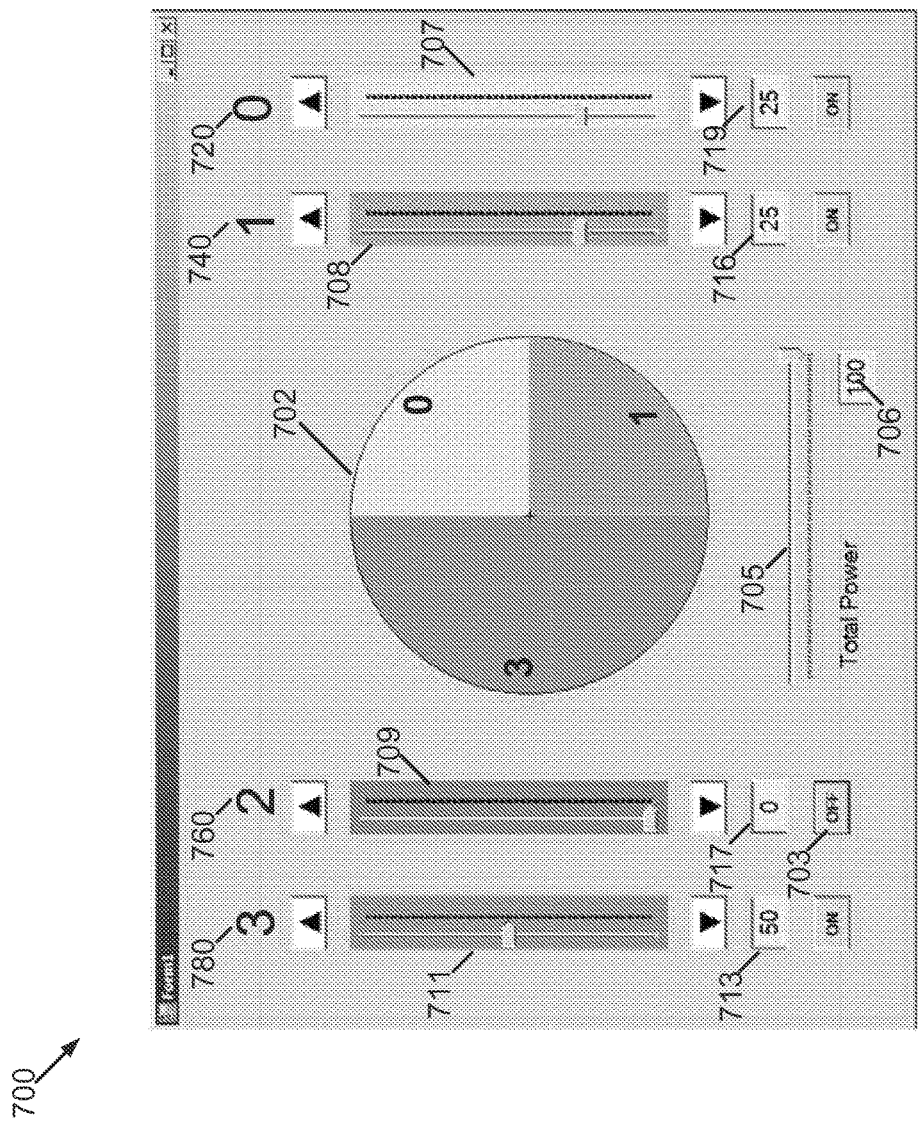
FIG. 7 depicts an example GUI and illustrates use of a toggle button to disable one of four electromagnetic energy sources.

FIG. 7 depicts an example GUI 700 and illustrates use of a toggle button 703 to disable one of four electromagnetic energy sources. A total output power for the four electromagnetic energy sources is set at 100% of a maximum total output power, as indicated by text box 706, total-power slider 705, and a radius of a pie-graph 702 that is at a maximum value. In the example GUI 700 of FIG. 7, four single-source controllers 720, 740, 760, 780 are labeled 0, 1, 2, and 3, respectively, and are associated with electromagnetic energy sources having these number designations. As indicated at the single-source controller 760, source 2 has been disabled via the toggle button 703, which is configured to turn the source off or on when pressed, depending on the current state of the source. The disabled state of source 2 is indicated at a text box 717 and via a position of a handle on a single-source slider 709. Further, the disabled state of source 2 is also indicated at the pie-graph 702, which does not include a sector corresponding to the source 2. In an example system, a source may only be disabled by pressing a toggle button, as in FIG. 7. In this example, using sliders 707, 708, 709, 711 or up/down arrow buttons of the single-source controllers 720, 740, 760, 780 can be used to decrease the percentage of the total output power to a minimum value (e.g., 1%), but the sliders or the up/down arrow buttons cannot be used to eliminate all output from a source.

Disabling source 2 via the toggle button 703 causes a corresponding power change in source 3, as indicated at single-source controller 780. At the single-source controller 780, a text box 713 indicates that source 3 is now contributing 50% of the total output power of the four sources. Because source 2 was contributing 25% of the total output power prior to being disabled, the 25% decrease in the output power contributed by the source 2 causes a 25% increase in the total output power contributed by the source 3. The increased contribution of the source 3 is also indicated via a position of a handle of a single-source slider 711. In the example of FIG. 7, changing the percentage of the output power contributed by a particular source affects only the percentage of the output power contributed by a single other source, such that a percentage of the total output power contributed by sources 0 and 1 are not changed, as indicated at the single-source controllers 720, 740. At the single-source controllers 720, 740, sliders 707, 708 and text boxes 716, 719 indicate that the sources 0 and 1 continue to contribute 25% of the total output power and are not affected by the disabling of source 2.

Figure 8:
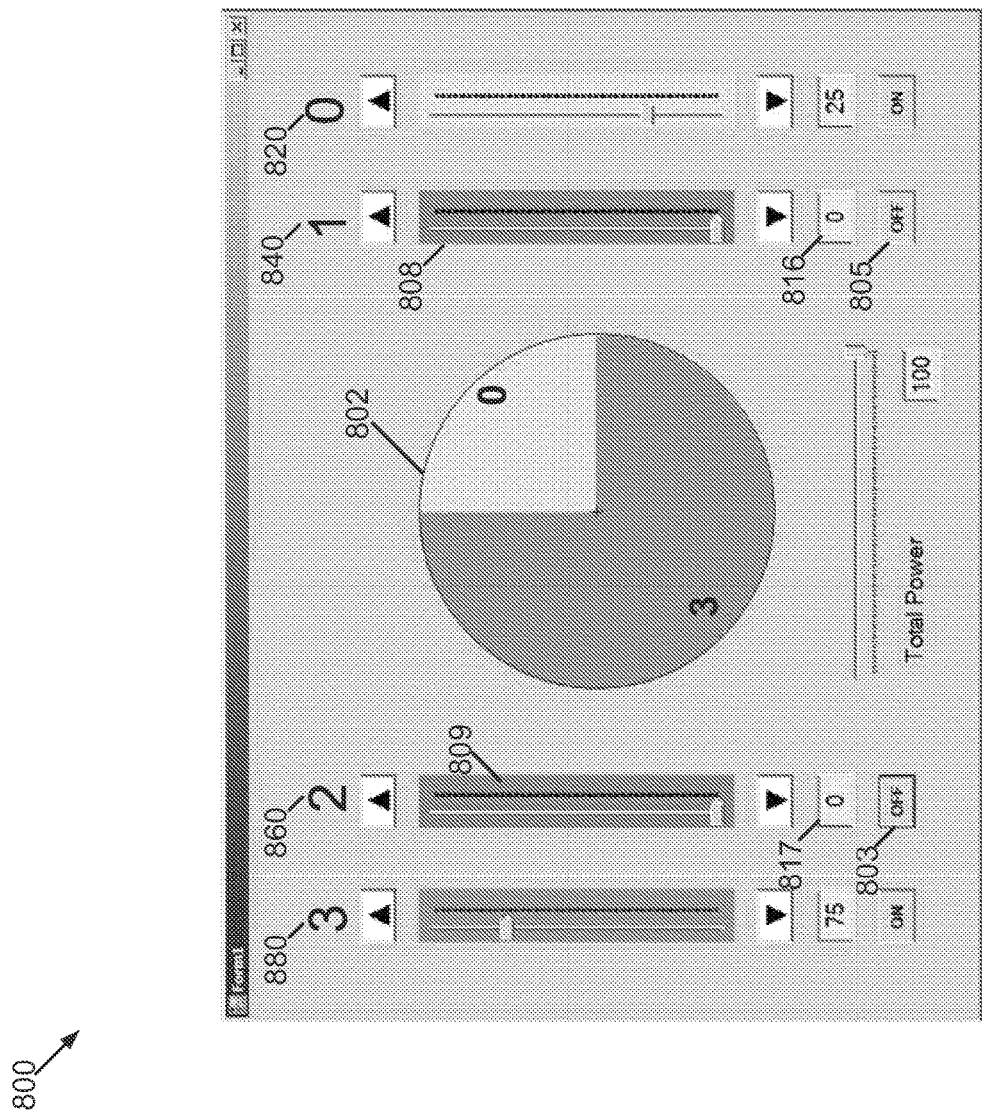
FIG. 8 depicts an example GUI illustrating two active electromagnetic energy sources and two disabled electromagnetic energy sources.

FIG. 8 depicts an example GUI 800 illustrating two active electromagnetic energy sources and two disabled electromagnetic energy sources. In the example GUI 800 of FIG. 8, four single-source controllers 820, 840, 860, 880 are labeled 0, 1, 2, and 3, respectively, and are associated with electromagnetic energy sources having these number designations. As indicated at the single-source controllers 860 and 840, sources 1 and 2 have been disabled via toggle buttons 803, 805. The disabled state of sources 1 and 2 are indicated at text boxes 816, 817 and via positions of handles of single-source sliders 808, 809. A pie-graph 802 also illustrates that sources 1 and 2 are disabled and includes sectors corresponding to sources 0 and 3 only.

Figure 9:
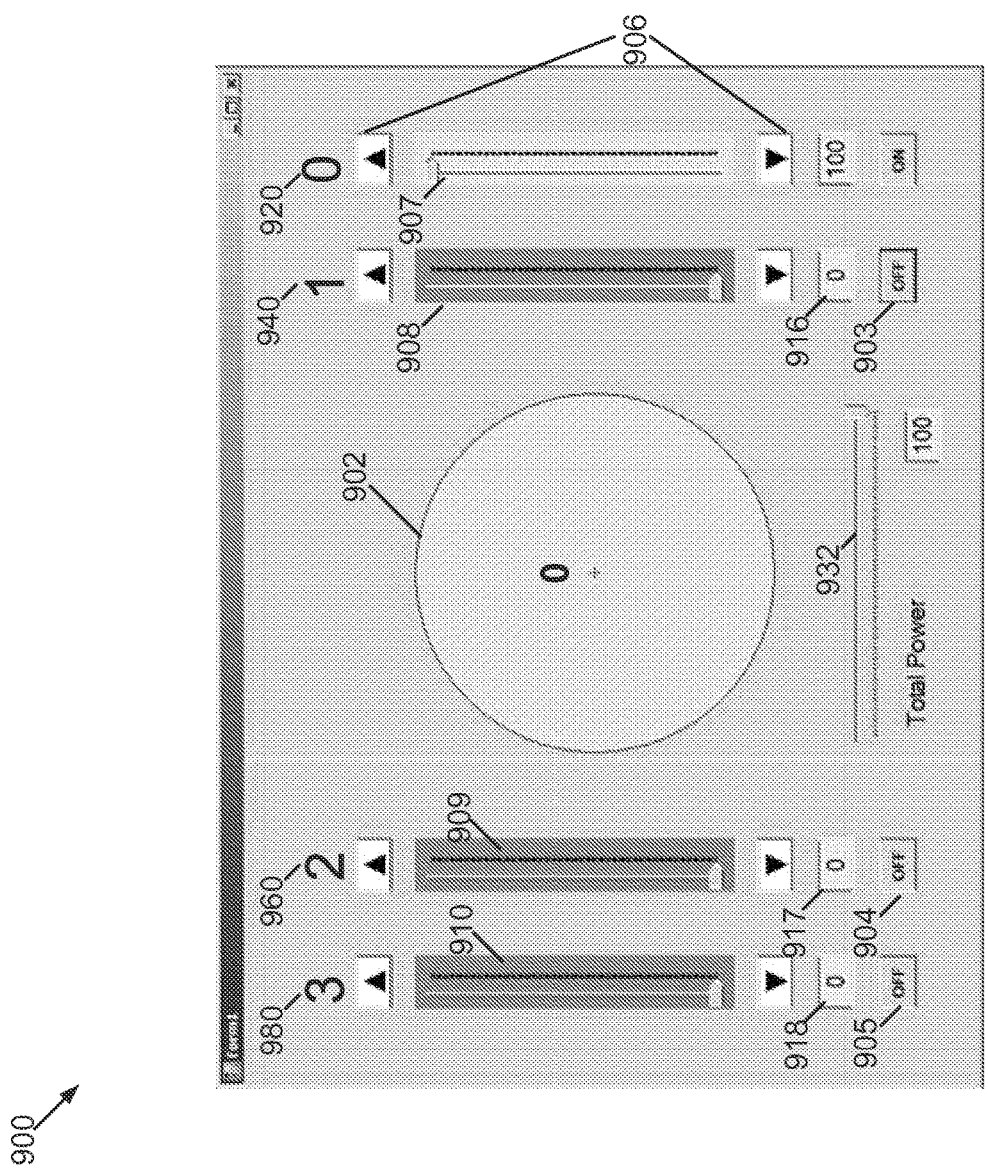
FIG. 9 depicts an example GUI illustrating single-laser operation.

FIG. 9 depicts an example GUI 900 illustrating single-laser operation. In the example GUI 900 of FIG. 9, four single-source controllers 920, 940, 960, 980 are labeled 0, 1, 2, and 3, respectively, and are associated with electromagnetic energy sources having these number designations. As indicated at the single-source controllers 940, 960, 980, sources 1, 2, and 3 have been disabled via toggle buttons 903, 904, 905. The disabled state of sources 1, 2, and 3 are indicated at text boxes 916, 917, 918 and via positions of handles of single-source sliders 908, 909, 910. A pie-graph 902 also illustrates that sources 1, 2, and 3 are disabled and includes only a sector corresponding to source 0. In this example, only the total output power for the four sources can be adjusted. In the single-source controller 920 for source 0, a single-source slider 907 and up/down buttons 906 are disabled, such that a percentage of the total output power contributed by the source 0 cannot be adjusted. Rather, only a handle of a total-power slider 932 can be adjusted to change the total output power, which changes the output power of the single source that is active, source 0.

Figure 10:
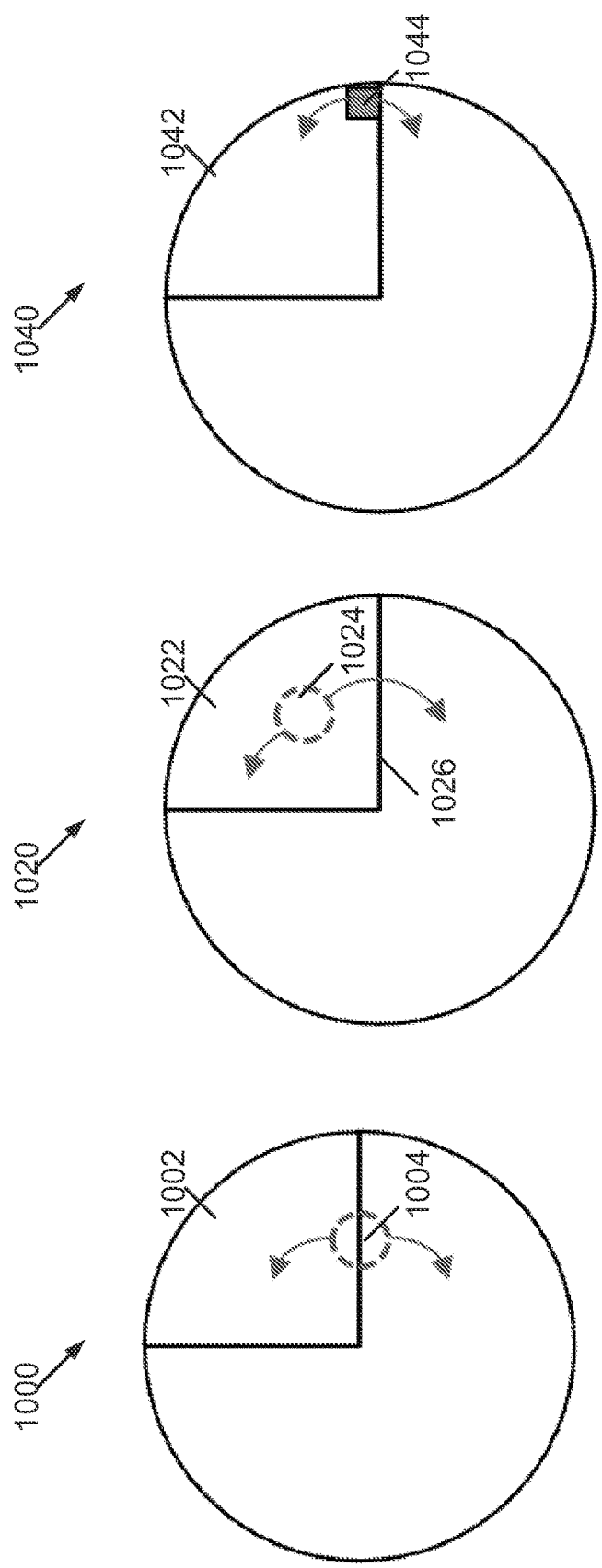
FIG. 10 illustrates methods of manipulating a sector of a pie-graph to change a percentage of a total output power contributed by a particular source.

FIG. 10 illustrates methods of manipulating a sector of a pie-graph to change a percentage of a total output power contributed by a particular source. As explained above with respect to the preceding figures, a pie-graph portion of a GUI may include a plurality of sectors (i.e., pie pieces) that indicate a percentage of the total output power contributed by each of the plurality of the electromagnetic energy sources. Thus, a particular electromagnetic energy source is associated with a particular sector of the pie-graph, with the particular sector having an angle that indicates the percentage of the total output power contributed by the particular source. Changing the angle modifies the percentage of the total output power contributed by the particular source.

In a pie-graph 1000 of FIG. 10, an angle of a sector 1002 is changed by dragging-and-dropping a point 1004 on a partition between the sector 1002 and an adjacent sector. In a pie-graph 1020, an angle of a sector 1022 is changed by dragging-and-dropping a point 1024 within an area of the sector 1022. Changing the angle of the sector 1022 in this manner does not involve manipulating any part of the partition 1026 between the sectors. In a pie-graph 1040, a resize box 1044 is used to change an angle of a sector 1042. The resize box 1044 may be located at a perimeter area of the pie-graph 1040, and a drag-and-drop action may be performed at the resize box 1044 to change the angle of the sector 1042.

Figure 11:
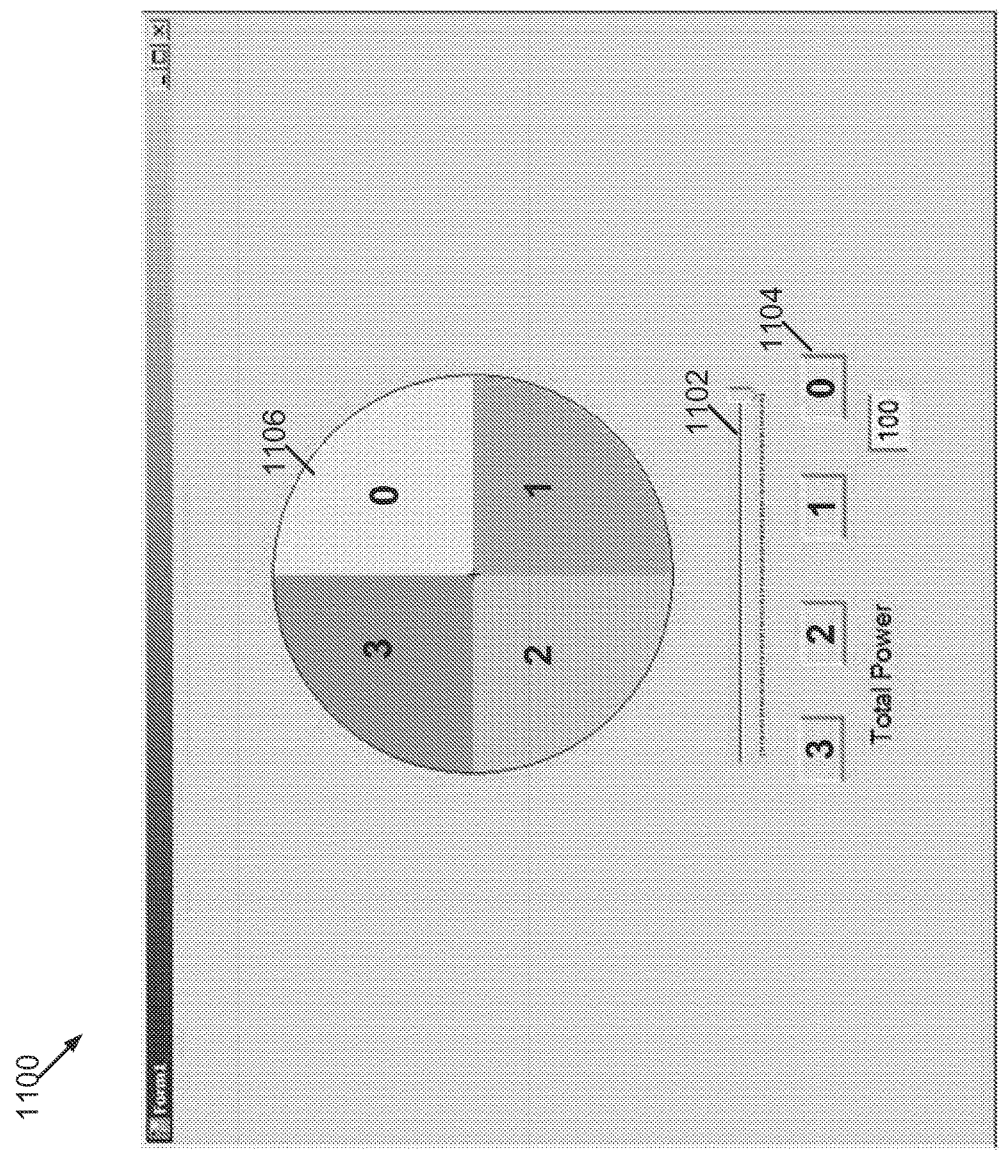
FIG. 11 depicts an example GUI where single-source controllers have been eliminated, and a single slider and a set of buttons are used to adjust an output of four electromagnetic energy sources.

FIG. 11 depicts an example GUI 1100 where single-source controllers have been eliminated, and a single slider 1102 and a set of buttons 1104 are used to adjust an output of four electromagnetic energy sources. The GUI 1100 of FIG. 11 includes a pie-graph 1106 configured to control a total output power of the four electromagnetic energy sources. The pie-graph 1106 includes a radius that indicates the total power output of the four sources and a plurality of sectors that indicate a percentage of the total output power contributed by each of the four electromagnetic energy sources. Rather than include a plurality of single-source controllers (e.g., including sliders and buttons configured to control a percentage of the total output power contributed by a particular source of the four electromagnetic energy sources), the example of FIG. 11 includes the single slider 1102 and the set of buttons 1104. When one button of the set of buttons 1104 is pressed, the slider 1102 can be used to adjust the percentage of the total output power contributed by a particular source associated with the pressed button. For example, to adjust the percentage of the total output power contributed by a source 0, a button numbered 0 is pressed, and the slider 1102 can then be used to adjust the output power of source 0. When no buttons are depressed, the slider 1102 can be used to adjust the combined, total output power of the four sources.

Figure 12:
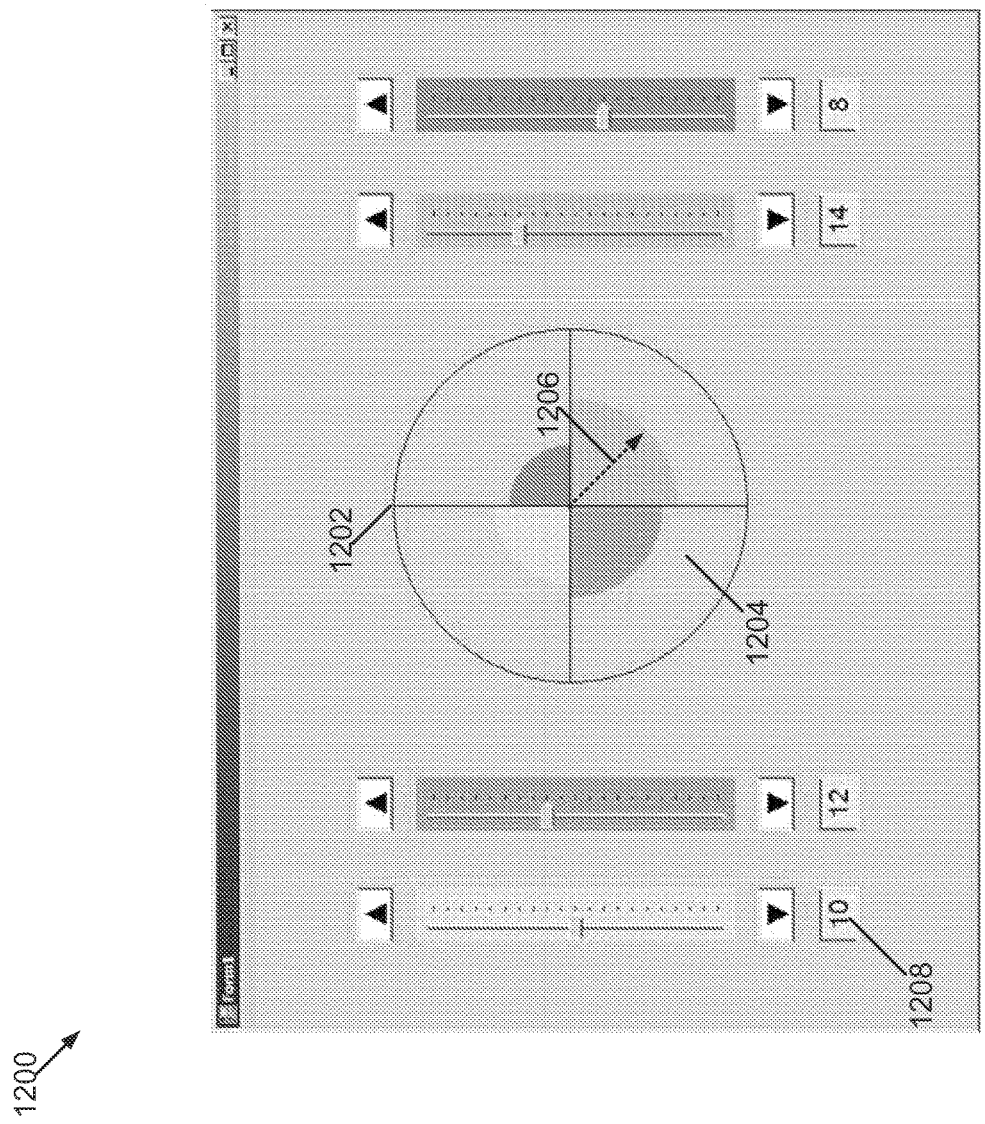
FIG. 12 depicts an example GUI including a pie-graph with a plurality of sectors, where a radius of a sector indicates an output power of a particular electromagnetic energy source.

FIG. 12 depicts an example GUI 1200 including a pie-graph 1202 with a plurality of sectors 1204, where a radius 1206 of a sector indicates an output power of a particular electromagnetic energy source. In preceding figures, an angle of a sector of a pie-graph indicated power output of a particular source. In FIG. 12, by contrast, the radius 1206 of the sector is used to indicate this. FIG. 12 also differs from preceding figures in that text boxes 1208 are used to indicate an actual output power of a particular source, rather than a percentage of the total output power for the particular source. In the example of FIG. 12, each of the sources have a maximum output power of 20 watts, and numbers in the text boxes 1208 indicate the actual output power of each of the sources in watts. Although no total-power slider or text box indicating the total output power is included in the example of FIG. 12, in other examples, the total-power slider or the text box may be included to allow display or adjustment of the total output power.

Figure 13:
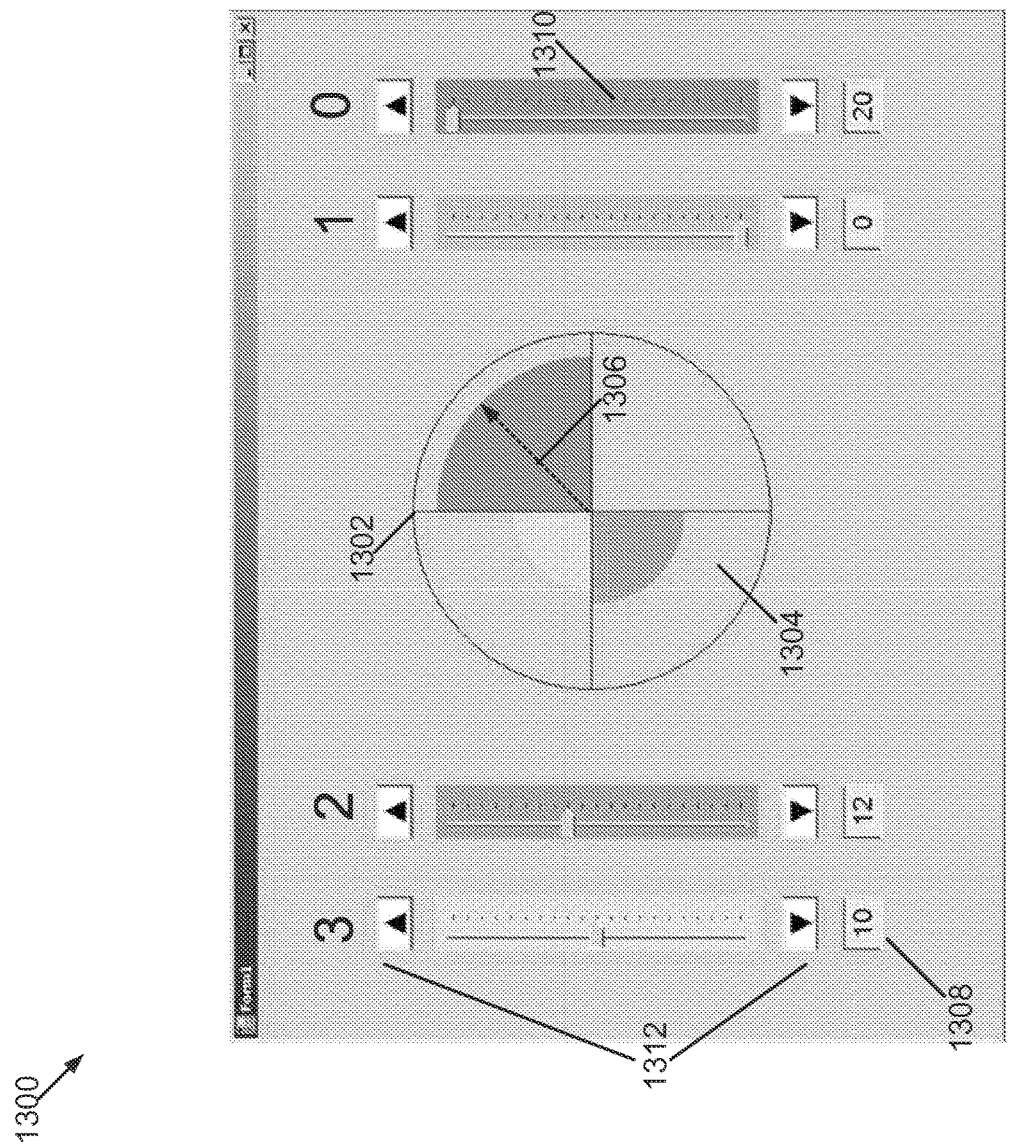
FIG. 13 depicts another example GUI including a including a pie-graph with a plurality of sectors, where a radius of a sector indicates output power of a particular electromagnetic energy source.

FIG. 13 depicts another example GUI 1300 including a pie-graph 1302 with a plurality of sectors 1304, where a radius 1306 of a sector indicates output power of a particular electromagnetic energy source. As in FIG. 12, the radius 1306 of the sector is used to indicate output power of a particular electromagnetic energy source, and text boxes 1308 are used to indicate an actual output power of the particular source in watts. In the GUI 1300 of FIG. 13, source 1 has been disabled, and source 0 has been set to output a maximum output power of 20 watts. These adjustments were made either by adjusting handles of slide bars 1310, by manipulating sectors 1304 of the pie-graph 1302 (e.g., by dragging-and-dropping a portion of a sector in a radial direction to modify the radius 1306 of the sector), or by pressing up/down buttons 1312.

Figure 14:
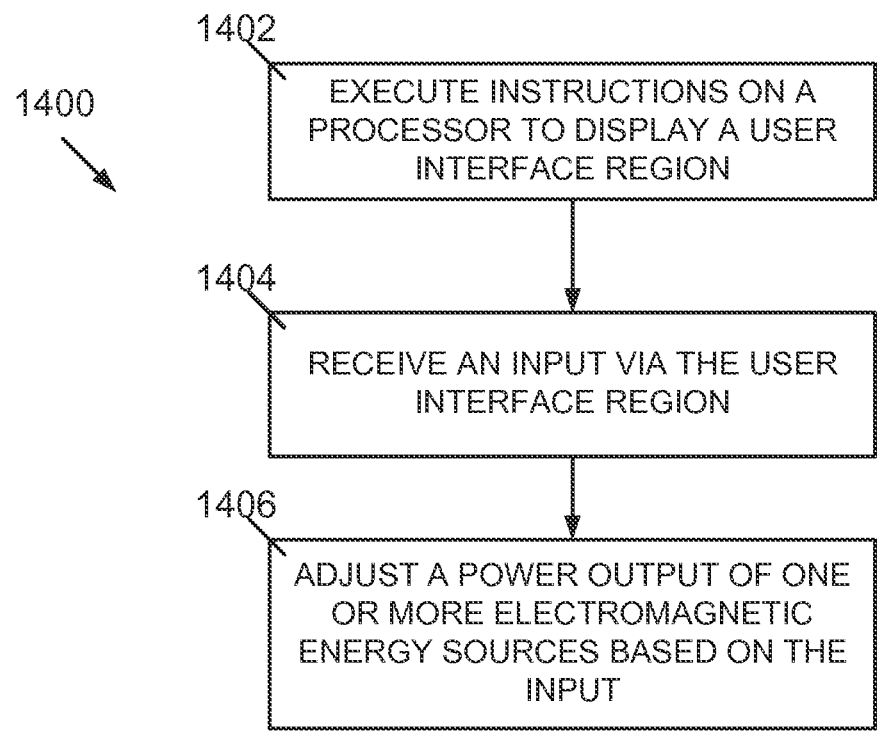
FIG. 14 is a flowchart illustrating a method for controlling a plurality of electromagnetic energy sources.

FIG. 14 is a flowchart illustrating a method for controlling a plurality of electromagnetic energy sources. At 1402, instructions are executed on a processor to display on a computer-human interface display device a user interface region. The user interface region includes a pie-graph configured to display a total output power of the plurality of the electromagnetic energy sources. The pie-graph includes a radius that indicates the total output power and a plurality of sectors that are configured to indicate percentages of the total output power contributed by each of the plurality of the electromagnetic energy sources. At 1404, an input is received via the user interface region, where the input is an interaction with the pie-graph that changes one of the radius or a sector of the plurality of the sectors. At 1406, a power output of one or more of the electromagnetic energy sources is adjusted based on the input.

This written description uses examples to disclose the invention, including the best mode, and also to enable a person skilled in the art to make and use the invention. The patentable scope of the invention may include other examples. Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Further, as used in the description herein and throughout the claims that follow, the meaning of "each" does not require "each and every" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive of may be used to indicate situations where only the disjunctive meaning may apply.

It is claimed:

1. An apparatus including at least one processor for controlling a plurality of laser sources, comprising:
a controller executed in the processor coupled to the plurality of laser sources, the controller configured to individually control a power output of each of the laser sources independently, based at least in part on an input received from a user through a user interface;
a computer-human interface display device displaying the user interface comprising a user interface region including user-selectable preset programs with output powers tailored for performing specific procedures,
the user interface region configured and arranged to display one or more parameters of the system and to receive the input comprising the user's interaction with at least a portion of the user interface region; and
a master controller executed in the processor and rendered on the user interface region, the master controller comprising a user-adjustable element of the user interface region configured as a virtual interface to the controller wherein based at least in part on the user's interaction with the master controller, the controller is configured and arranged to adjust at least one of the parameters and control an update to at least a portion of the user interface region indicating a resulting operational status of the system, the update including a display of at least one of the parameters and at least one resulting operational status of the system; and wherein the display of at least one of the parameters is adjusted automatically based at least in part on at least one of the user's selection of preset programs and interaction with the master controller;
a pie graph configured to display the total output power of the plurality of the laser sources, the pie graph including a radius that indicates the total output power and a plurality of sectors that indicate percentages of the total output power contributed by each of the plurality of the laser sources;
wherein the pie graph and controller are configured such that: a) changing the radius of the pie graph changes the total output power of the plurality of the electromagnetic energy sources; and b) changing the one of the radius or the sector of the plurality of the sectors changes a percentage of the total output power contributed by one or more of the plurality of the laser sources and adjusts the power output of at least one of the plurality of the laser sources relative at least another of the plurality of the laser sources.

2. The apparatus of claim 1, wherein the controller executed in the processor is configured and arranged to adjust the power output of one or more of the electromagnetic energy sources based at least in part on the input, wherein the input includes a user's interaction with the user interface.

3. The apparatus of claim 1:
wherein the user interface region includes a total-power slider including a handle that is configured to move along a predetermined path to control the total output power of the plurality of the electromagnetic energy sources, and wherein a position of the handle on the predetermined path indicates the total output power.

4. The apparatus of claim 3, wherein the user interface region further includes:
a text box indicating the total output power, wherein a number in the text box indicates the total output power as a percentage of a maximum output power of the plurality of the electromagnetic energy sources.

5. The apparatus of claim 4, wherein the number in the text box is configured to change in response to the moving of the handle on the total-power slider.

6. The apparatus of claim 5, wherein the position of the handle changes in a manner that is not proportional to changes in the total output power.

7. The apparatus of claim 6, wherein the position of the handle change changes according to a logarithmic scale.

8. The apparatus of claim 1, further comprising:
receiving a second input via the user interface region, the second input being an interaction with one or more of a plurality of single-source controllers of the user interface region, wherein at least one of the plurality of single-source controllers executed in the processor is configured to control a percentage of the total output power contributed by a particular source of the plurality of the electromagnetic energy sources.

9. The apparatus of claim 8, wherein changing the percentage of the total output power contributed by the particular source changes a percentage of the total output power contributed by one or more of the other sources of the plurality of the electromagnetic energy sources.

10. The apparatus of claim 8, wherein one or more of the single-source controllers includes:
a single-source slider including a handle that is configured to move along a predetermined path to control the percentage of the total output power contributed by the particular source, wherein a position of the handle along the predetermined path indicates the percentage of the total output power contributed by the particular source.

11. The apparatus of claim 8, wherein one or more of the plurality of single-source controllers includes:
a set of buttons, the set of buttons including a first button that is configured to increase the percentage of the total output power contributed by the particular source when pressed and a second button that is configured to decrease the percentage of the total output power contributed by the particular source when pressed.

12. The apparatus of claim 8, wherein one or more of the plurality of single-source controllers includes:
a toggle button or toggle switch configured to turn off or turn on the particular source when pressed.

13. The apparatus of claim 8, wherein one or more of the single-source controllers includes:
a text box including a number that indicates the percentage of the total output power contributed by the particular source.

14. The apparatus of claim 13, wherein a sum of the numbers of the text boxes for the plurality of the single-source controllers is equal to 100.

15. The apparatus of claim 8, wherein the interaction with the one or more of the plurality of the single-source controllers causes a change of an angle of a sector of a pie-graph displayed on the user interface, the pie-graph indicating a level of power of at least one of the of the plurality of the electromagnetic energy sources.

16. The apparatus of claim 15, wherein an interaction with the pie-graph that changes the sector of a plurality of the sectors causes a change in one or more of the plurality of the single-source controllers.

17. The apparatus of claim 1, further comprising:
receiving a second input via the user interface region, the second input being an interaction with a multi-source slider of the user interface region, wherein the multi-source slider includes a handle that is configured to move along a predetermined path to control the percentages of the total output power contributed by each of the plurality of the electromagnetic energy sources, and wherein the multi-source slider controls a percentage of the total output power contributed by a particular source of the plurality of the electromagnetic energy sources based on an activation of a toggle button that is associated with the particular source;
adjusting the power output of one or more of the electromagnetic energy sources based on the second input.

18. The apparatus of claim 1, wherein changing the total output power changes an output power of each of the plurality of the electromagnetic energy sources.

19. The apparatus of claim 18, wherein changing the total output power by a particular percentage value causes a corresponding change in the output power of each of the plurality of the electromagnetic energy sources by the particular percentage value.

20. The apparatus of claim 1, wherein each of the plurality of the electromagnetic energy sources is configured to generate electromagnetic radiation of a different wavelength.

21. The apparatus of claim 20, wherein the different wavelengths of the plurality of the electromagnetic energy sources are configured to be used in performing different actions.

22. The apparatus of claim 21, wherein the plurality of the electromagnetic energy sources are configured to perform a dental procedure, and wherein the different actions include killing bacteria, whitening teeth, cutting tissue, healing tissue, or curing a composite material.

23. A system for controlling a plurality of electromagnetic energy sources, comprising:
one or more processors;
one or more computer-readable non-transitory storage mediums containing instructions configured to cause the one or more processors to perform operations including:
displaying on a computer-human interface display device a user interface region, the user interface region including:
a master controller executed in the processor and rendered on the user interface region, the master controller comprising a user-adjustable element configured and arranged to adjust at least one parameter and control an update to at least a portion of the user interface region, the update including a display of at least one parameter and at least one operational status of the system; and
wherein the display of at least one parameter is adjusted automatically based at least in part on at least one of the user's selection of preset programs and interaction with the master controller:
a pie-graph configured to display a total output power of the plurality of the electromagnetic energy sources, the pie-graph including a radius that indicates the total output power and a plurality of sectors that indicate percentages of the total output power contributed by each of the plurality of the electromagnetic energy sources;
receiving an input via the user interface region, the input being an interaction with the pie-graph that changes one of the radius or a sector of the plurality of the sectors; and
adjusting a power output of one or more of the electromagnetic energy sources based on the input.

24. A computer-program product for controlling a plurality of electromagnetic energy sources, tangibly embodied in a machine-readable storage non-transitory medium, including instructions configured to cause a data processing apparatus to:
display on a computer-human interface display device a user interface region, the user interface region including:
a master controller executed in the processor and rendered on the user interface region, the master controller comprising a user-adjustable element configured and arranged to adjust at least one parameter and control an update to at least a portion of the user interface region, the update including a display of at least one parameter and at least one operational status of the system; and
wherein the display of at least one parameter is adjusted automatically based at least in part on at least one of the user's selection of preset programs and interaction with the master controller:
a pie-graph configured to display a total output power of the plurality of the electromagnetic energy sources, the pie-graph including a radius that indicates the total output power and a plurality of sectors that indicate percentages of the total output power contributed by each of the plurality of the electromagnetic energy sources;
receive an input via the user interface region, the input being an interaction with the pie-graph that changes one of the radius or a sector of the plurality of the sectors; and adjust a power output of one or more of the electromagnetic energy sources based on the input.

* * * * *